(12) United States Patent
Shih et al.

(10) Patent No.: US 9,017,646 B2
(45) Date of Patent: Apr. 28, 2015

(54) PROCESS OF EVALUATING BLOOD-BRAIN BARRIER PERMEABILITY OF STROKE RAT BY USING FLUORESCENT SUBSTANCE

(75) Inventors: Jun-Ming Shih, Taoyuan County (TW); Yuan-Ruei Huang, Taoyuan County (TW); Yu-Lung Wu, Taoyuan County (TW); Shih-Ying Lee, Taoyuan County (TW); Kang-Wei Chang, Taoyuan County (TW); Chia-Chien Chen, Taoyuan County (TW)

(73) Assignee: Institute of Nuclear Energy Research, Atomic Energy Council, Lungtan, Taoyuan (TW)

( * ) Notice: Subject to any disclaimer, the term of this patent is extended or adjusted under 35 U.S.C. 154(b) by 302 days.

(21) Appl. No.: 13/545,238

(22) Filed: Jul. 10, 2012

(65) Prior Publication Data

US 2014/0017173 A1  Jan. 16, 2014

(51) Int. Cl.
*A61K 49/00* (2006.01)
*A61B 5/00* (2006.01)

(52) U.S. Cl.
CPC .......... *A61K 49/0017* (2013.01); *A61B 5/0071* (2013.01)

(58) Field of Classification Search
None
See application file for complete search history.

(56) References Cited

U.S. PATENT DOCUMENTS 6,936,827 B1 * 8/2005 Mohler ...................... 250/458.1

OTHER PUBLICATIONS

Belayev et al. Quantitative evaluation of blood-brain barrier permeability following middle cerebral artery occlusion in rats. 1996 Brain Res. 739: 88-96.*
Yao et al. Evans blue dye-enhanced capillary-resolution photoacoustic microscopy in vivo. 2009 J. Biomed. Opt. 14: 054049.*

* cited by examiner

*Primary Examiner* — Michael G Hartley
*Assistant Examiner* — Jennifer Lamberski
(74) *Attorney, Agent, or Firm* — Jackson IPG PLLC; Demian K. Jackson

(57) ABSTRACT

A process of evaluating blood-brain barrier permeability of a stroke rat by using fluorescent substance is disclosed. This process uses an Evans blue dye having spontaneous fluorescence properties, in combination with the use of a new non-invasive in vivo imaging system (IVIS), to obtain fluorescent signals so as to assess the change in the blood-brain barrier permeability of rodents after a cerebral artery stroke model surgery. In operation, an Evans blue dye is injected into a stroke rat of middle cerebral artery occlusion model. A non-invasive in vivo imaging system is used to detect the fluorescence distribution of the whole brain, and obtain images combined by the fluorescence images and optical images for the whole brain tissue. Thereby, the change in the blood-brain barrier permeability of the stroke rat can be completely realized.

5 Claims, 3 Drawing Sheets

PROCESS OF EVALUATING BLOOD-BRAIN BARRIER PERMEABILITY OF STROKE RAT BY USING FLUORESCENT SUBSTANCE

BACKGROUND OF THE INVENTION

1. Field of the Invention

The present invention relates to a process of evaluating blood-brain barrier permeability of a stroke rat by using fluorescent substance. Particularly, this invention relates to an evaluation process which can assess the change in the blood-brain barrier permeability of rodents after a cerebral artery stroke model surgery. More particularly this invention relates to an evaluation process which can prove the location of the brain injury is fully consistent with the damaged region of the blood-brain barrier.

2. Description of Related Art

An Evans blue dye has high affinity to the albumin in the blood. The albumin cannot enter the brain through the blood-brain barrier. For this reason, the Evans blue dye is often used to assess the blood-brain barrier permeability. The Evans blue dye can be excited to emit fluorescence. Currently, the evaluation of the change in the blood-brain barrier permeability of a single section of brain tissue is performed by means of fluorescence detection using a fluorescence microscope, which cannot obtain the fluorescence imaging of the whole brain.

The conventional technology which is only capable of observing the fluorescence for the single section of brain tissue by viewing the brain slices through the fluorescent microscopy cannot provide the user with the fluorescence imaging of the whole brain required in actual use. Therefore, there is a need of a novel process of evaluating the blood-brain barrier permeability of a stroke rat, which meets the user's need.

SUMMARY OF THE INVENTION

This present invention aims at overcoming the shortages of the prior art and providing a novel process which can detect the fluorescence distribution over the whole brain and assess the change in the blood-brain barrier permeability of rodents after a cerebral artery stroke model surgery. Furthermore, this invention aims at providing a process of evaluating the blood-brain barrier permeability of a stroke rat by using fluorescent substance.

In order to achieve the above and other objectives, the process of evaluating the blood-brain barrier permeability of a stroke rat by using fluorescent substance includes injecting a Evans blue dye into a stroke rat of middle cerebral artery occlusion model; detecting the fluorescence distribution of the whole brain by using a non-invasive in vivo imaging system; and obtaining images combined by the fluorescence images with optical images for the whole brain tissue.

DETAILED DESCRIPTION OF THE PREFERRED EMBODIMENTS

The aforementioned illustrations and following detailed descriptions are exemplary for the purpose of further explaining the scope of the present invention. Other objectives and advantages related to the present invention will be illustrated in the subsequent descriptions and appended tables.

Figure 1:
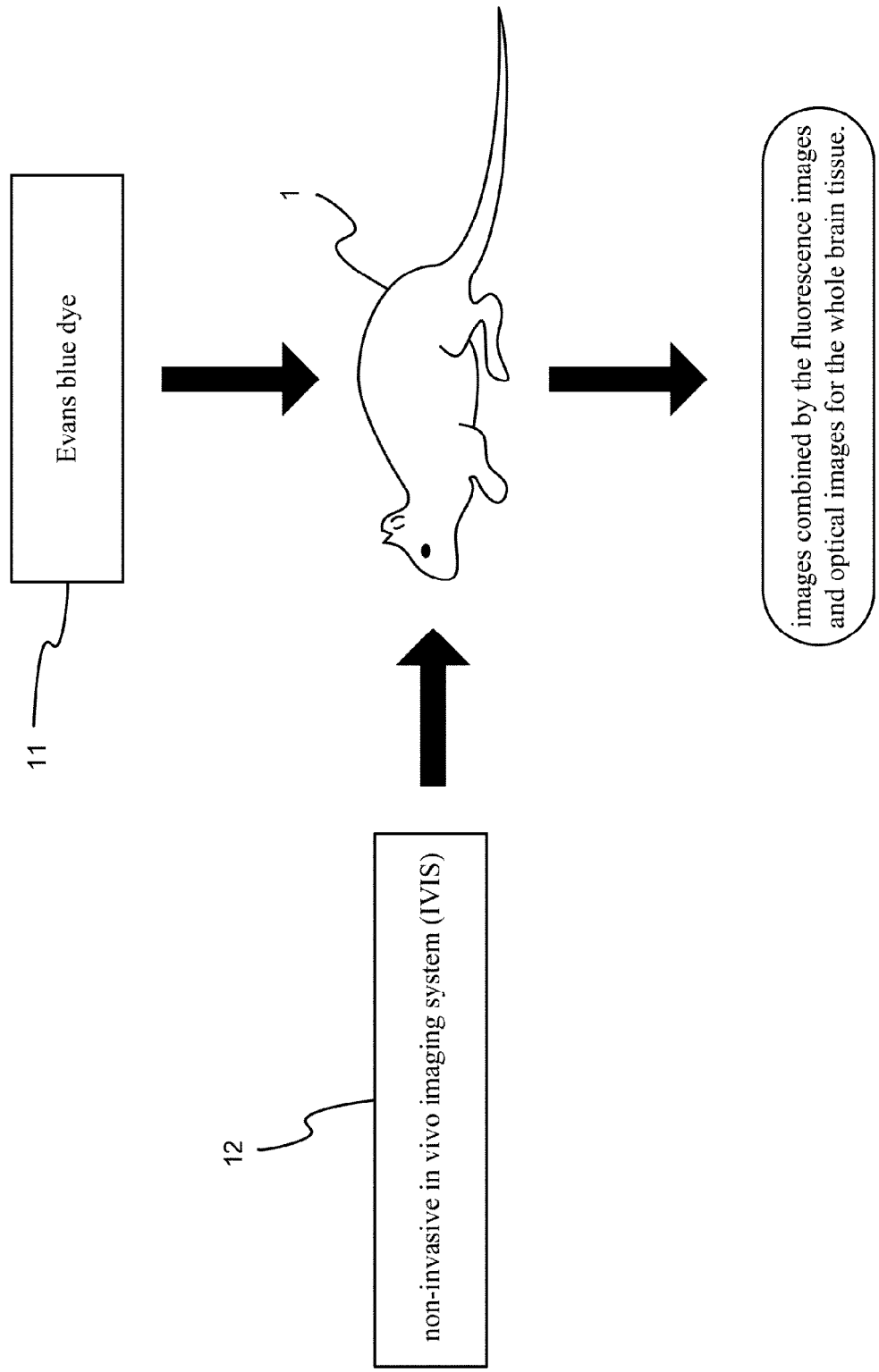
FIG. 1 is a schematic view of an evaluation process of the present invention.

FIG. 1 is a schematic view of an evaluation process of the present invention. As shown, the invention is a process of evaluating the blood-brain barrier permeability of a stroke rat by using fluorescent substance. The process of the invention uses Evans blue dye having spontaneous fluorescence properties, in combination with the use of a new non-invasive in vivo imaging system (IVIS), to obtain fluorescent signals so as to assess the change in the blood-brain barrier permeability of rodents after a cerebral artery stroke model surgery. In operation, an Evans blue dye 11 is injected into a stroke rat 1 of middle cerebral artery occlusion model. A non-invasive in vivo imaging system 12 is used to detect the fluorescence distribution of the whole brain, and obtain images combined by the fluorescence images and optical images for the whole brain tissue. Thereby, the change in the blood-brain barrier permeability of the stroke rat can be completely realized.

Figure 2:
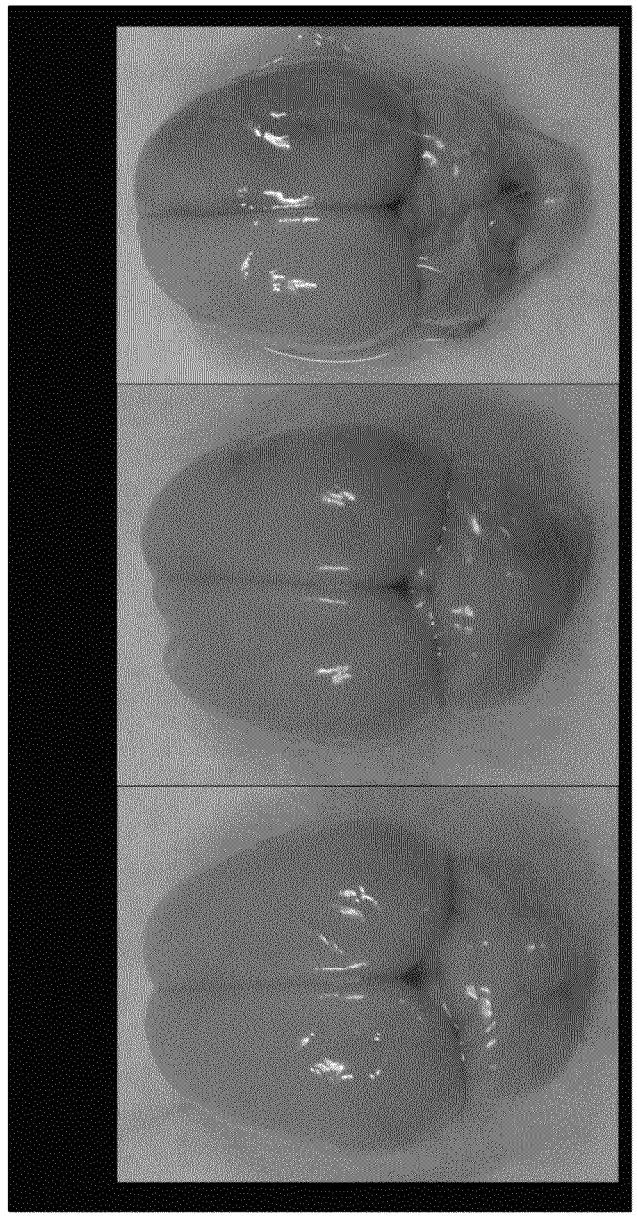
FIG. 2 is an optical image of the whole brain tissue after the injection of Evans blue dye according to the invention.
Figure 3:
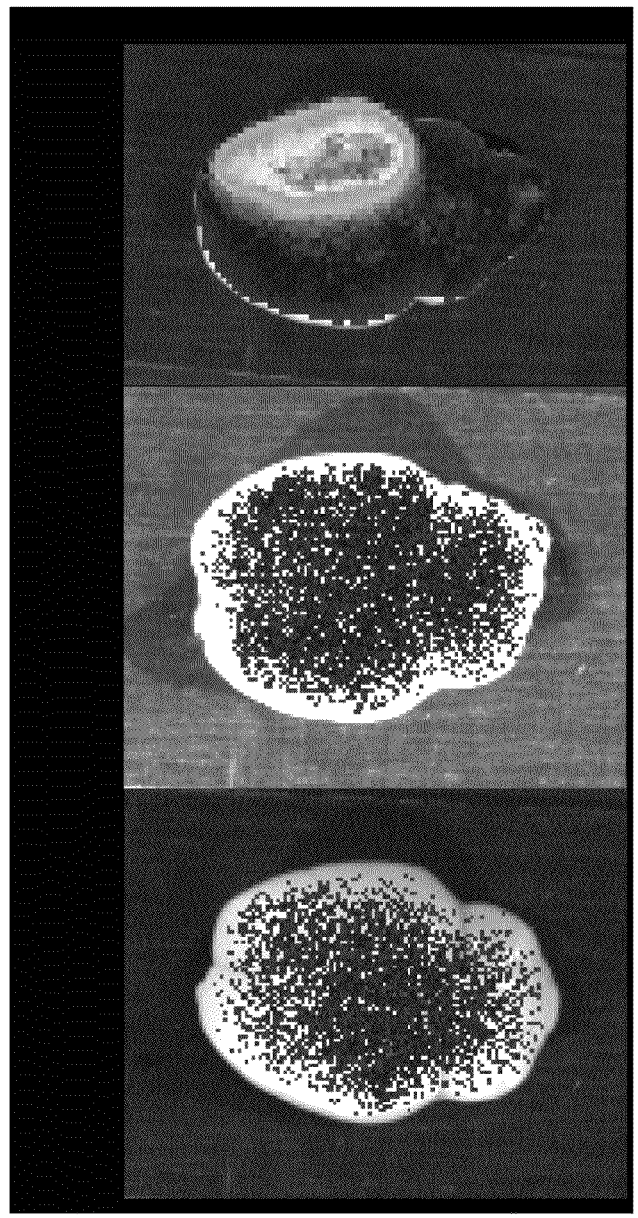
FIG. 3 is an integrated image combined the fluorescence images with the optical images by using an IVIS 100 system according to the invention.

FIG. 2 is an optical image of the whole brain tissue after the injection of Evans blue dye according to the invention. FIG. 3 is an integrated image combined the fluorescence images with the optical images by using an IVIS 100 system according to the invention. As shown, in a preferred embedment, the invention uses a SD (Sprague Dawley) rat as the stroke animal model subject to transient bilateral common carotid artery and right middle cerebral artery ligation. After the rat is anesthetized, the surgery procedure is described roughly as follows. The skull of the rat is opened by drilling in order to find the right middle cerebral artery. A 10-0 needle is used to take the right middle cerebral artery and rotate it 90 degrees. It is ensured that the blood cannot flow smoothly under the observation by a microscope. Then, both sides of the common carotid artery are subject to ligation for 90 minutes. After the stitches have been removed, wounds are sutured to allow the rat to be recovered.

Three groups are provided in the experiment, in which a sham group is a rat whose skull is opened without the bilateral common carotid artery and right middle cerebral artery ligation so as to exclude the impact caused by drilling the skull; a control group is the blank rat without any surgery; and a surgery group is a stroke rat whose skull is opened to perform the middle cerebral artery ligation.

Evans blue dye is dissolved in saline and injected intravenously into the rat via its tail 24 hours after surgery. After distribution for 30 minutes, the rat is anesthetized for transcardial perfusion in order to wash away the dye within the blood vessels. The brain tissue is carefully taken and subject to digital camera photography (as shown in FIG. 2). The IVIS 100 (Caliper) system is used to detect the fluorescence distribution of the whole brain tissue. The Evans blue dye can be excited by the light of 620 nanometer (nm) wavelengths to emit the light of 680 nm wavelength which can be detected by the IVIS 100 system and further converted into images (as shown in FIG. 3).

After the injection of Evans blue dye in intravenous way via the rat's tail 24 hours after stroke surgery, the dye will leak into the interstitial cells of the right brain. As shown at the right side of FIG. 2, the blue part represents the blue dye. The control group as shown at the left side of FIG. 2 and the sham group as shown at the middle of FIG. 2 show no presence of the blue dye in the brain tissue. Furthermore, 24 hours of stroke after surgery, fluorescence signals are detected in the right brain.

The location where emits the fluorescence can be found by integration of the optical images and the fluorescence images, which is consistent with the location of the blue dye as shown at the right side of FIG. 3, and also fully consistent with the part which is subject to the middle cerebral artery ligation. For the control group as shown at the left side of FIG. 3 and the sham group as shown in the middle of FIG. 3, fluorescence is not obvious in the brain tissue.

Therefore, the present invention can prove that the location of the brain injury is fully consistent with the damaged region of the blood-brain barrier by obtaining the clear image of the whole brain. It is also confirmed that after the stroke, the blood-brain barrier permeability deteriorates and allows the dye which originally cannot enter the brain to flow into the damaged brain area.

In this way, the present invention has successfully established a novel technology platform which can detect the relative position of the photoluminescence of the whole brain. It is a convincing proof that the dye which should not exist at the location where the brain injury occurs but after stroke it can flow into that location. It means the stroke will destroy the blood-brain barrier permeability.

In summary, the process of evaluating the blood-brain barrier permeability of a stroke rat by using fluorescent substance according to the present invention effectively improves the shortcomings of the prior art. The Evans blue dye is injected into the rat of cerebral artery occlusion model rat. The non-invasive in vivo imaging system (IVIS) is used to detect the fluorescence distribution over the whole brain. Thereby, the change in the blood-brain barrier permeability of the stroke rat can be completely understood.

The descriptions illustrated supra set forth simply the preferred embodiments of the present invention; however, the characteristics of the present invention are by no means restricted thereto. All changes, alternations, or modifications conveniently considered by those skilled in the art are deemed to be encompassed within the scope of the present invention delineated by the following claims.

What is claimed is:

1. A process of evaluating blood-brain barrier permeability of a rat model of stroke by using a fluorescent substance, the process comprising:
    injecting an Evans blue dye as the fluorescent substance into a rat model of stroke, wherein the rat model of stroke has been subjected to middle cerebral artery occlusion;
    taking the brain from the rat; and then
    detecting the fluorescence distribution in the whole brain by using a non-invasive in vivo imaging system; and
    obtaining both fluorescence images and optical images for the whole brain tissue.

2. The process of claim 1, wherein the rat model of stroke is subjected to transient bilateral common carotid artery and right middle cerebral artery ligation.

3. The process of claim 1, wherein the fluorescence images and the optical images of the whole brain tissue enable identification of where damage has occurred in the brain.

4. The process of claim 1, wherein the dye is injected into the rat tail.

5. The process of claim 1, further comprising identifying the location of the fluorescence by integration of the optical and fluorescent images.

* * * * *